United States Patent

Kawamukai et al.

Patent Number: 5,853,611
Date of Patent: Dec. 29, 1998

[54] POLYETHER POLYMER, PREPARATION PROCESS AND USE THEREOF

[75] Inventors: Hiroshi Kawamukai; Katsuhiko Rindo; Takashi Oda, all of Wakayama; Masaaki Moriyama; Hideyuki Hanazawa, both of Chiba; Yasushi Kajihara, Ibaraki, all of Japan

[73] Assignee: Kao Corporation, Tokyo, Japan

[21] Appl. No.: 894,556

[22] PCT Filed: Feb. 9, 1996

[86] PCT No.: PCT/JP96/00291

§ 371 Date: Sep. 11, 1997

§ 102(e) Date: Sep. 11, 1997

[87] PCT Pub. No.: WO96/26233

PCT Pub. Date: Aug. 29, 1996

[30] Foreign Application Priority Data

Feb. 24, 1995 [JP] Japan ................................ 7-036681
Apr. 6, 1995 [JP] Japan ................................ 7-081112

[51] Int. Cl.$^6$ ............................ C11D 9/30; C08F 283/04
[52] U.S. Cl. ............................ 252/89; 528/271; 528/354; 528/361; 528/363; 528/366; 528/370; 525/423; 525/426; 525/435; 525/540; 252/117; 252/174.21; 252/174.23; 252/DIG. 2; 424/78.08; 424/78.37; 424/70.01; 424/70.11
[58] Field of Search ..................... 528/354, 361, 528/363, 366, 370, 271; 525/423, 426, 435, 540; 252/89, 117, 174.21, 174.23, DIG. 2; 424/78.08, 78.37, 70.01, 70.11

[56] References Cited

U.S. PATENT DOCUMENTS

| | | |
|---|---|---|
| 3,960,782 | 6/1976 | Daley et al. ........................... 252/544 |
| 4,013,787 | 3/1977 | Varlerberghe et al. ................... 424/70 |
| 4,032,565 | 6/1977 | Kilpatrick et al. ...................... 560/147 |
| 4,123,378 | 10/1978 | Abel et al. .............................. 252/171 |
| 4,189,468 | 2/1980 | Vanlerberghe et al. .................. 424/70 |
| 4,277,581 | 7/1981 | Vanlerberghe et al. ................. 525/420 |
| 4,445,521 | 5/1984 | Crollier et al. ............................. 132/7 |
| 4,971,789 | 11/1990 | Vanlerberghe et al. .................. 424/70 |
| 5,656,586 | 8/1997 | Li et al. .................................. 510/535 |

FOREIGN PATENT DOCUMENTS

| | | |
|---|---|---|
| A 0 649 834 | 4/1995 | European Pat. Off. . |
| A 2 285 414 | 4/1976 | France . |
| A 2 359 165 | 2/1978 | France . |
| A 2 695 033 | 3/1994 | France . |
| A 27 32 178 | 1/1978 | Germany . |
| A 2 080 303 | 2/1982 | United Kingdom . |

OTHER PUBLICATIONS

AN 79–09557b Derwent Publications Ltd., London, GB; Mar. 24, 1978, abstract.

*Primary Examiner*—Samuel A. Acquah
*Attorney, Agent, or Firm*—Oblon, Spivak, McClelland, Maier & Neustadt, P.C.

[57] ABSTRACT

The present invention relates to a polyether polymer having structural units represented by general formula (1), wherein $R^1$ and $R^2$ mean individually an alkyl group of 1–20 carbon atoms, which may have at least one hydroxyl group, and Y denotes an alkylene group of 1–10 carbon atoms, which may have a hydroxyl group, a preparation process thereof, and a moisturizer, a cosmetic composition and a detergent composition comprising this polymer. The cosmetic composition and detergent composition are excellent in moisture retention, keep up the moisturizing effect over a long period of time and give users a pleasant feeling.

10 Claims, No Drawings

POLYETHER POLYMER, PREPARATION PROCESS AND USE THEREOF

TECHNICAL FIELD

The present invention relates to a novel polyether polymer, and particularly to a polyether polymer having carbobetaine groups on its side chains, a preparation process thereof, its use for a moisturizer, and a cosmetic composition and a detergent composition comprising the polymer.

BACKGROUND ART

Various kinds of moisturizers have heretofore been incorporated in many cosmetic and detergent compositions for the purpose of imparting a moisturized feeling to the user's hair and skin. Low-molecular weight compounds such as glycerol, propylene glycol, sorbitol, urea and adducts of alkylene oxide with saccharides have been used as such moisturizers.

However, none of these moisturizers have been satisfactory from the viewpoint of moisture retention, a feeling upon use, etc., and involved a problem that they are easily diffused and washed away by sweat and/or water, and so their effects do not last long. In addition, when they are used in cosmetic compositions which are washed off after their use, such as rinses and body rinses, or in detergent compositions containing a great amount of a surfactant, they are almost washed off, and so their inherent effects cannot be fully exhibited in many cases.

High-molecular weight moisturizers such as collagen, hyaluronic acid and cationized cellulose have also been known. However, these moisturizers are not fully satisfactory from the viewpoint of a feeling upon use because they give a sticky feeling to the user's hair and skin or they give less moisturized feeling.

On the other hand, a moisturizer of the carboxybetaine type is disclosed in EP-A-0649834. However, such a compound has also been diffused and washed away by sweat and/or water like the moisturizers of the low-molecular weight compounds, and so the lastingness of its moisturizing effect has not been sufficient.

There has thus been a demand for development of a moisturizer which has excellent moisture retention, gives users a pleasant feeling and keeps up its moisturizing effect over a long period of time without being washed away by sweat and/or water or even after washing off it.

DISCLOSURE OF THE INVENTION

In view of the foregoing circumstances, the present inventors have carried out an extensive investigation. As a result, it has been found that when the side chains, or chloromethyl groups, of polyepichlorohydrin are reacted with an amine, and then with a ω-halocarboxylic acid (salt) or a cyclic lactone, a polyether polymer having carbobetaine groups on its side chains is obtained, and this polymer not only has excellent moisture retention, but also keeps up its moisturizing effect over a long period of time and gives users a pleasant feeling when incorporated for use in various cosmetic and detergent compositions, thus leading to completion of the present invention.

It is therefore an object of the present invention to provide a new polyether polymer and a process for its preparation.

A further object is to provide a new moisturizer having advantageous properties.

A still further object is to provide a cosmetic composition.

A still further object is to provide a detergent composition.

According to the present invention, there is thus provided a polyether polymer having structural units represented by the following general formula (1):

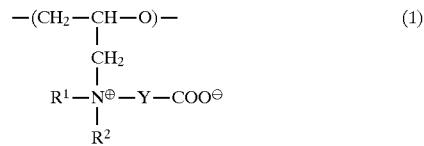

wherein $R^1$ and $R^2$ mean individually an alkyl group of 1–20 carbon atoms, which may have one or more hydroxyl groups, and Y denotes an alkylene group of 1–10 carbon atoms, which may have a hydroxyl group.

According to the present invention, there is also provided a process for preparing a polyether polymer having structural units represented by the general formula (1):

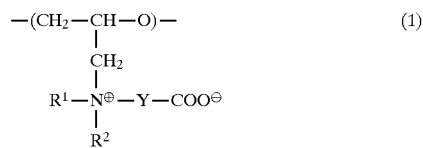

wherein $R^1$ and $R^2$ mean individually an alkyl group of 1–20 carbon atoms, which may have one or more hydroxyl groups, and Y denotes an alkylene group of 1–10 carbon atoms, which may have a hydroxyl group, which comprises reacting a polymer having structural units represented by the general formula (2):

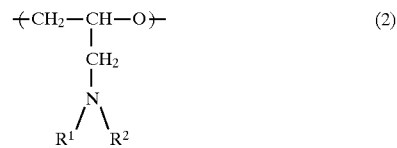

wherein $R^1$ and $R^2$ have the same meaning as defined above, with a ω-halocarboxylic acid or a salt thereof represented by the following general formula (3) or a cyclic lactone represented by the following general formula (4):

wherein Y has the same meaning as refined above, Z denotes a halogen atom, M is a metal ion or a hydrogen atom, and m stands for a number of 1–8.

According to the present invention, there is further provided a moisturizer comprising, as an active ingredient, the polyether polymer having the structural units represented by the general formula (1).

According to the present invention, there is still further provided use of the polyether polymer having the structural units represented by the general formula (1) for a moisturizer.

According to the present invention, there is yet still further provided a cosmetic composition comprising the polyether polymer having the structural units represented by the general formula (1).

According to the present invention, there is yet still further provided a detergent composition comprising the polyether polymer having the structural units represented by the general formula (1), and detergent ingredients.

BEST MODE FOR CARRYING OUT THE INVENTION

The polyether polymer according to the present invention is required only to have the structural units represented by the general formula (1) in its molecule and may be either a polymer composed simply of such structural units or a copolymer with those having other side chains in this structural unit, or with one or more kinds of other structural units. In the case of the copolymer, those having different side chains in the structural unit represented by the general formula (1) may be bonded to each other in the form of either a block copolymer or a random copolymer, or it does not also care about the bonding configuration of the principal chain in the copolymer, i.e., whether the principal chain is formed by head-to-tail linkage or by head-to-head linkage.

In the general formula (1), $R^1$ and $R^2$ mean individually an alkyl group of 1–20 carbon atoms, which may have at least one hydroxyl group. Specific examples thereof include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, 2-hydroxyethyl, 3-hydroxypropyl, 4-hydroxybutyl, 5-hydroxypentyl, 6-hydroxyhexyl, 7-hydroxyheptyl, 8-hydroxyoctyl, 9-hydroxynonyl, 10-hydroxydecyl, 11-hydroxyundecyl, 12-hydroxydodecyl, 13-hydroxytridecyl, 14-hydroxytetradecyl, 15-hydroxypentadecyl, 16-hydroxyhexadecyl, 17-hydroxyheptadecyl, 18-hydroxyoctadecyl, 19-hydroxynonadecyl, 20-hydroxyeicosyl, 2,3-dihydroxypropyl and 2,3,4,5-tetrahydroxypentyl groups, and the like. Of these, alkyl groups of 1–5 carbon atoms, which may have at least one hydroxyl group, are preferred, with 2-hydroxyethyl, 3-hydroxypropyl, 4-hydroxybutyl, 5-hydroxypentyl, 2,3-dihydroxypropyl, methyl, ethyl, propyl, butyl and pentyl being particularly preferred. $R^1$ and $R^2$ may be identical with or different from each other. In particular, it is preferred that $R^1$ be an alkyl group having 1–5 carbon atom, while $R^2$ be a ω-hydroxyalkyl group having 1–5 carbon atoms.

Examples of the alkylene group of 1–10 carbon atoms, which is indicated by Y and may have a hydroxyl group, include methylene, ethylene, propylene, trimethylene, tetramethylene, pentamethylene, hexamethylene, heptamethylene, octamethylene, nonamethylene, decamethylene, hydroxymethylene, hydroxyethylene and hydroxymethylmethylene groups, and the like. Of these, those having 1–5 carbon atoms are preferred, with methylene and ethylene groups being particularly preferred.

Specific examples of the structural unit represented by the general formula (1) include those represented by the following formulae (a) to (d):

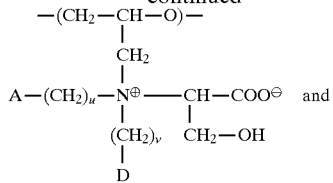 (a)

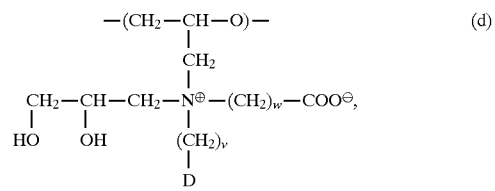 (b)

 (c)
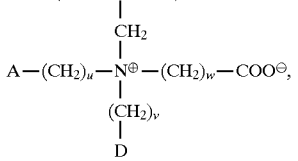 and

 (d)
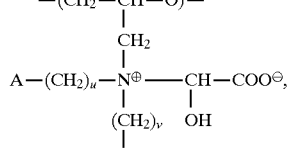

wherein A and D mean, independently of each other, a hydrogen atom or a hydroxyl group, u and v are, independently of each other, a number of 1–20, and w is a number of 1–10.

In the above formulae, it is preferred that u and v be, independently of each other, a number of 1–5 when A and/or D is OH. It is also preferred that w be a number of 1–5.

Of these, a structural unit represented by the following formula (a-1), (a-2), (a-3) or (d-1) is more preferred.

 (a-1)
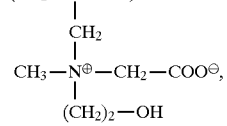

 (a-2)
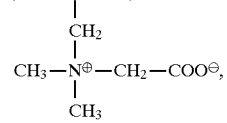

 (a-3)
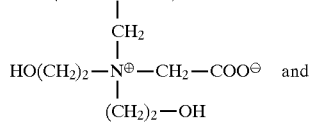 and

 (d-1)
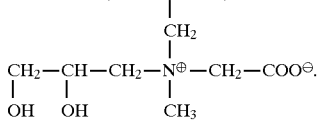

The polyether polymer according to the present invention may be a copolymer composed of the structural unit represented by the general formula (1) [hereinafter referred to as the structural unit (1)] and one or more structural units other than this structural unit. The other structural units may preferably be etheric structural units. Examples thereof include those represented by the following formulae (e) to (i) [hereinafter referred to as the structural units (e) to (i), respectively].

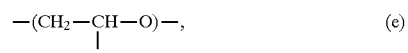 (e)

-continued

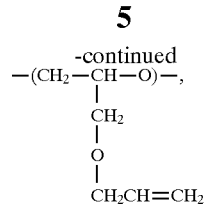 (f)

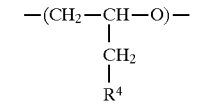 (g)

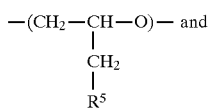 (h)

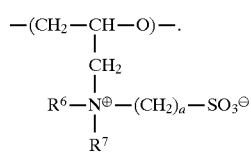 (i)

In the formula (e), $R^3$ means —H, —$CH_3$, —$CH_2OH$, —$CH_2$—O—$CH_2CH(OH)$ —$CH_2OH$, —$CH_2OR^8$, —$CH_2SR^8$ or —$CH_2S(CH_2)_3SR^8$ in which $R^8$ is an alkyl, alkenyl, cycloalkyl, aralkyl or aryl group having 1–20 carbon atoms.

In the formula (g), $R^4$ denotes a cationic group represented by the following formula (g-1), (g-2) or (g-3):

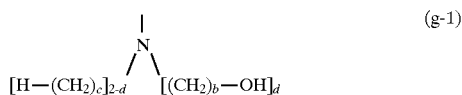 (g-1)

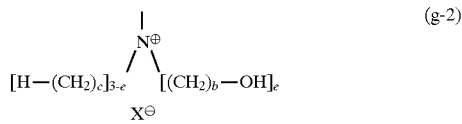 (g-2)

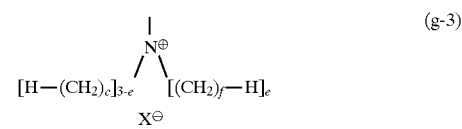 (g-3)

wherein b and c are individually a number of 1–10, d is a number of 0–2, e is a number of 0–3, f is a number of 1–20, and $X^-$ denotes a counter anion.

In the formula (h), $R^5$ means —$SO_3M$ or —O—$CH_2$—COOM in which M is a metal ion such as sodium or potassium, or a hydrogen atom.

In the formula (i), $R^6$ and $R^7$ mean individually an alkyl group of 1–20 carbon atoms, which may have one or more hydroxyl groups, and a is a number of 1–10.

As the counter anion $X^-$, a halogen ion such as a chlorine or bromine ion, a methylsulfate ion or an ethyl-sulfate ion is preferred.

Of these structural units, the structural units (e), (g) and (h) are more preferred. With respect to the structural unit (e), those, in which $R^3$ is —H, —$CH_2OH$ or —$CH_2$—O—$R^{8'}$ ($R^{8'}$: an alkyl or aryl group having 6–18 carbon atoms), are preferred. With respect to the structural unit (g), those, in which $R^4$ is a group represented by any one of the following formulae:

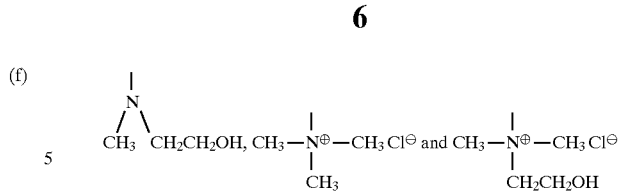

are preferred. With respect to the structural unit (h), those, in which M is a sodium atom, are preferred.

In a polymer or a copolymer of the structural unit (1), which may contain one or more of the structural units (e) to (i), it is preferred that the structural unit (1) be contained in a proportion of 10–100 wt. %, particularly 50–100 wt. % based on the total weight of the copolymer. It is also preferred that the structural units (e) and (f) be contained in proportions of 0–90 wt. %, and the structural units (g), (h) and (i) be contained in proportions of 0–50 wt. %.

These other structural units can be introduced by a process in which their corresponding oxirane compounds are copolymerized with epichlorohydrin, a process in which an epichlorohydrin (co)polymer is subjected to a functional group conversion reaction in accordance with the conventional method, or the like.

Among such copolymers, copolymers composed of the structural unit (1) and the structural unit (e), (g), (h) or (i) are preferred, with copolymers composed of the structural unit (1) and the structural unit (e) and/or (g) being particularly preferred.

The polyether polymer according to the present invention preferably has a weight-average molecular weight of 500–1,000,000, more preferably 1,000–500,000, most preferably 5,000–100,000. Any (co)polymer having a weight-average molecular weight within this range is preferred because it has high moisturizing ability and gives users a pleasant feeling.

The polyether polymer according to the present invention can be prepared by reacting a polymer (aminated polyepichlorohydrin) having structural units represented by the general formula (2) with a ω-halocarboxylic acid or a salt thereof (3), or a cyclic lactone (4) in accordance with, for example, the following reaction scheme:

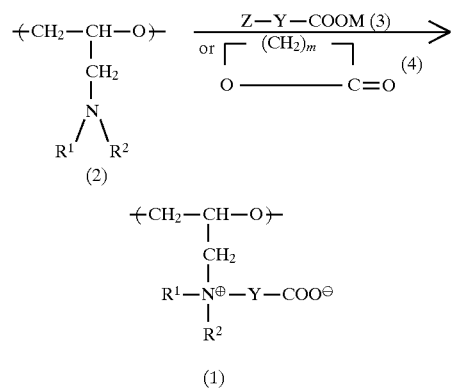

wherein m stands for a number of 1–8, and $R^1$, $R^2$, Y, Z and M have the same meaning as defined above.

The aminated polyepichlorohydrin (2) as used herein can be obtained by using polyepichlorohydrin or its copolymer with one or more other structural units, and a secondary amine to conduct an amination reaction in accordance with, for example, the process described in DE U.S. Pat. No. 2,540,310. A (co)polymer corresponding to the aminated polyepichlorohydrin (2) can be synthesized by reacting polyepichlorohydrin or its copolymer with one or more other structural units and a primary amine, and then reacting the resultant product with ethylene oxide.

The polyepichlorohydrin can be synthesized in accordance with, for example, the process described in Journal of Polymer Science, Polymer Chemistry Edition, Vol. 13, 1993 (1975). For example, epichlorohydrin is polymerized at room temperature to 40° C. in the presence of a polymerization catalyst composed of triethylaluminum and water in chlorobenzene as a solvent, whereby polyepichlorohydrin can be obtained. Besides, the copolymer with the other structural units can be obtained by copolymerizing epichlorohydrin with, for example, a monomer such as ethylene oxide or allyl glycidyl ether in an autoclave. As the polyepichlorohydrin or the copolymer of epichlorohydrin and another monomer, there may be used commercially-available products such as Gechron® 1000, Gechronr® 2000 and Gechron® 3102 (products of Nippon Zeon Co., Ltd.); Epichlomer® H, Epichlomer® C and Epichlomer® CG (products of Daiso Co., Ltd.); and Herclor® H and Herclor® C (products of Hercules Inc.). These polymers such as polyepichlorohydrin preferably have a weight-average molecular weight of 2,000–1,500,000 from the viewpoint of handling and achievement of good properties.

The secondary amine used in the amination reaction may have at least one primary or secondary hydroxyl group. Examples thereof include dimethylamine, diethylamine, methylethylamine, methyethanolamine, diethanolamine and secondary amines synthesized by reacting an oxirane compound such as epichlorohydrin or glycidol with a primary amine such as methylamine. These secondary amines are preferably used in an amount of generally 1–10 equivalents to the chlorine content in the polyepichlorohydrin. As the primary amine, there may be used methylamine, ethylamine, propylamine or the like. The primary amine is preferably used in an amount of 1–10 equivalents to the chlorine content in the polyepichlorohydrin. In order to sebsequently add ethylene oxide to the reaction product of the primary amine, ethylene oxide may be used in an amount of 1–10 equivalents per equivalent of the amine.

Examples of a reaction solvent used in the amination reaction include protonic or aprotic polar solvents such as acetonitrile, water, methanol, ethanol, chloroform, tetrahydrofuran, dimethylformamide, dimethyl sulfoxide and N-methylpyrrolidone, and nonpolar solvents such as toluene and xylene. Dimethylformamide, dimethyl sulfoxide, N-methylpyrrolidone and the like, which are polar aprotic solvents, as well as toluene and xylene, which are nonpolar solvents, are more preferred.

The reaction may preferably be conducted at 80°–150° C., particularly 90°–130° C. It is also preferable to conduct the reaction under pressure in an autoclave depending on the reaction conditions such as the use of an amine having a boiling point lower than ordinary temperature.

The aminated polyepichlorohydrin (2) thus obtained is reacted with a ω-halocarboxylic acid or a salt thereof (3), or a cyclic lactone (4) to form a betaine compound. Examples of the ω-halocarboxylic acid or the salt thereof (3) used herein include chloroacetic acid, sodium chloroacetate, potassium chloroacetate, 3-bromopropionic acid, sodium 3-bromopropionate, potassium 3-bromopropionate, 6-bromohexanoic acid, sodium 6-bromohexanoate, potassium 6-bromohexanoate, 11-bromoundecanoic acid, sodium 11-bromoundecanoate and potassium 11-bromoundecanoate. These compounds are preferably used in an amount of generally 1–5 equivalents, particularly 1–2 equivalents to the aminated polyepichlorohydrin (2).

Examples of the cyclic lactone (4) include β-propiolactone, γbutyrolactone, δ-valerolactone and ε-caprolactone. These cyclic lactones are preferably used in an amount of 0.95–2 equivalents, particularly 0.98–1.02 equivalents to the aminated polyepichlorohydrin (2).

As the ω-halocarboxylic acid or the salt thereof (3), or the cyclic lactone (4), which is to be reacted with the aminated polyepichlorohydrin (2), ω-halocarboxylic acids having 2–7 carbon atoms, β-propiolactone and γ-butyrolactone are preferred.

In the reaction for forming the betaine compound, a polar protic solvent is used as a reaction solvent. Preferable examples thereof include water, alcohols (methanol, ethanol, 2-propanol, etc.), and mixed solvents composed of water and an alcohol.

The reaction is preferably conducted at 40°–100° C., particularly 60°–85° C.

After the amination reaction and/or the reaction of the formation of the betaine compound, the resulting polymer may also be treated with the conventional decoloring agent, for example, borohydride compounds such as sodium borohydride to improve the hue of the polymer.

Among the polyether polymers according to the present invention, the copolymers composed of the structural unit (1) and the other structural unit(s) can be prepared by using, as a starting material, a copolymer composed of epichlorohydrin and the,other structural unit(s) in a similar manner to that described above.

For example, a copolymer, which contains, as structural units, those in which $R^4$ in the structural unit (g) is represented by the formula (g-2), can be obtained by using, for example, polyepichlorohydrin as a starting material polymer to aminate the polymer in the same manner as described above, quaternizing side chains, or aminated functional groups, of the aminated polymer with a quaternizing agent such as an alkyl halide at the desired compositional ratio and then reacting the thus-quaternized product with a ω-halocarboxylic acid or a salt thereof, or a cyclic lactone.

Since the thus-obtained polyether polymers (1) according to the present invention have a function which combines moisture retention (water retention) with adsorptivity on the hair and skin, and also possess good hydrophilicity, they are useful as moisturizers.

Accordingly, a moisturizer according to the present invention, which comprises, as an active ingredient, the polyether polymer (1), gives users an excellent moisturized feeling and keeps up its effect over a long period of time when applied to the hair and/or skin, and can hence be used in various applications, e.g., cosmetic and detergent compositions.

One or more of the polyether polymers are incorporated into the cosmetic compositions according to the present invention. The polyether polymers are preferably incorporated in a proportion of 0.001–20 wt. % (hereinafter indicated merely by "%") based on the total weight of the composition. In particular, it is preferred that they be incorporated in a proportion of 0.05–10%, most preferably 0.1–5% because a proper moisturized feeling lasts for a long period of time.

In the cosmetic compositions according to the present invention, as needed, those routinely employed as cosmetic ingredients, for example, higher alcohols having a straight-chain or branched alkyl or alkenyl group; hydrocarbons such as liquid paraffin, vaseline and solid paraffin; lanolin derivatives such as liquid lanolin and lanolin fatty acid; phospholipids such as lecithin; sterols such as cholesterol, and derivatives thereof; collagenolytic peptide derivatives; fluorine-containing oily bases such as perfluoropolyether; oils and fats such as esters of higher alcohols with higher fatty acids, higher fatty acids and long-chain amidoamines having an alkyl or alkenyl group; animal and vegetable oils and fats such as mink oil and olive oil; nonionic surfactants, anionic surfactants, amphoteric surfactants and cationic surfactants; antidandruff agents such as zinc pyrithione and Octopirox (piroctone ethanolamine salt); disinfectants such as triclosan and triclocarban; antiinflammatory agents such as dipotassium glycyrrhetinate and tocopheryl acetate; medicinally-effective ingredients such as blood circulation-facilitating agents, skin activators and vitamins; antiseptics such as parabens; viscosity modifiers such as methylcellulose, ethylcellulose, hydroxycellulose, carboxyvinyl polymers, xanthan gum, guar gum and ethanol; colorants such as dyes and pigments; ultraviolet absorbents; other moisturizers such as propylene glycol, glycerol, carbitol, 3-methyl-1,3-butanediol and saccharides; astringents; perfume bases; coloring matters; etc., may be suitably incorporated in addition to the essential ingredient described above within limits not impeding the effects of the present invention.

The cosmetic compositions according to the present invention may be prepared in accordance with a method known per se in the art and may be formulated in any forms such as liquid, cream, solid and powder. However, it is particularly preferred that they be formulated in the form of liquid or cream.

One or more of the polyether polymers are incorporated into the detergent compositions according to the present invention. The polyether polymers are preferably incorporated in a proportion of 0.05–20% based on the total weight of the composition. In particular, it is preferred that they be incorporated in a proportion of 0.1–10%, most preferably 0.2–5% because a proper moisturized feeling lasts for a long period of time even after the composition is used in washing and washed off.

In the detergent compositions according to the present invention, detergent ingredients, usually, various kinds of surfactants employed in detergent compositions, may be optionally used within limits not impeding the effects of the present invention.

More specifically, examples of anionic surfactants to be used include sulfate and sulfonate type surfactants such as alkylsulfates, polyoxyethylene alkylsulfates, sulfosuccinates, taurates, isethionates and α-olefin-sulfonates; carboxylate type surfactants such as fatty acid soaps, ether carboxylate surfactants and acylated amino acid surfactants; and phosphate type surfactants such as alkylphosphates. Of these, the surfactants of the fatty acid soap, sulfate and isethionate types are particularly preferred from the viewpoint of a feeling upon use and foaming.

Examples of amphoteric surfactants include carbobetaine, sulfobetaine and imidazolium betaine type amphoteric surfactants. Hydroxypropylsulfobetaine, desalted secondary imidazolinium betaine and the like are preferably used.

Examples of nonionic surfactants include surfactants of the polyoxyalkylene-added type, polyoxypropylene- and polyoxyethylene-added type, amine oxide type, mono- or diethanolamide type, and polyhydric alcohol type such as sorbitan fatty acid esters, glycerol fatty acid esters sucrose fatty acid esters, alkylsaccharides and N-polyhydroxyalkyl fatty acid amides. In particular, nonionic surfactants of the amine oxide, diethanolamide and alkylsaccharide types are preferably used.

Examples of cationic surfactants include mono- or dialkyl-added quaternary ammonium salts having a straight-chain or branched alkyl group and alkylene oxide adducts thereof, said alkylene oxide being added to the alkyl group (s) of the ammonium salts. In particular, quaternary ammonium salts having a straight-chain monoalkyl group of 12–16 carbon atoms or a branched alkyl group of 20–28 carbon atoms are preferably used.

These surfactants may be used either singly or in any combination thereof and are preferably incorporated in a proportion of 2–60%, particularly 5–50% based on the total weight of the detergent composition.

Besides, these surfactants are preferably used in a proportion ranging from 5 to 10,000 parts by weight, particularly from 10 to 1,000 parts by weight per part by weight of the polyether polymer.

In the detergent compositions according to the present invention, other ingredients routinely employed in detergent compositions, for example, polyhydric alcohols such as ethylene glycol, polyethylene glycols, propylene glycol, polypropylene glycols, butylene glycols, glycerol, polyglycerols, sugar alcohols, etc.; oily ingredients, such as hydrocarbons such as liquid paraffin, squarane, vaseline and solid paraffin, natural oils such as olive oil, jojoba oil, evening primrose oil, coconut oil and beef tallow, ester oils such as isopropyl myristate, cetyl isooctanoate and neopentylglycol dicaprate, silicone oils such as dimethylsilicone and methylphenylsilicone, and higher fatty acids such as isostearic acid and oleic acid; medicinally-effective ingredients such as vitamins, disinfectants, antiinflammatory agents, antidandruff agents, activators, cold sensation-imparting agents and ultraviolet absorbents; water-swelling clay minerals such as montmorillonite, saponite, hectorite, beagum, cunivia and smectone; polymers, such as polysaccharides such as karrageenan, xanthan gum, sodium alginate, pullulan, methylcellulose, carboxymethylcellulose, hydroxyethylcellulose and hydroxypropylcellulose, and synthetic polymers such as carboxyvinyl polymers and polyvinyl pyrrolidone; pigments, such as inorganic pigments such as titanium oxide, kaolin, mica, sericite, zinc white and talc, and polymeric powders such as poly(methyl methacrylate) powder and nylon powder; antiseptics such as methylparaben and butylparaben; viscosity modifiers such as inorganic salts, polyethylene glycol stearate and ethanol; pearly luster-imparting agents; perfume bases; coloring matters; antioxidants; and the like, may be suitably incorporated in addition to the above ingredients within limits not impeding the effects of the present invention.

The detergent compositions according to the present invention may be prepared in accordance with a method known per se in the art and may be formulated in any forms such as liquid, paste, solid and powder. However, it is particularly preferred that they be formulated in the form of liquid or paste. The detergent compositions according to the present invention are preferably provided as detergents which have a possibility that they may come contact with the skin and/or the hair, such as skin detergents, hair detergents and diswashing detergents.

As described above, the polyether polymers according to the present invention have high water retention, adsorbability and hydrophilicity, and are hence useful not only for cosmetic composition and detergent compositions, but also for various chemicals, for example, flocculants, antistatic agents, surface modifiers, dispersants, anti-fogging agents, soiling preventives, etc., which are applied on the surface of various materials such as metals, glasses, ceramics and plastics.

EXAMPLES

The present invention will hereinafter be described more specifically by the following examples. However, the present invention is not intended to be limited to these examples.

Preparation Example 1

In an autoclave purged with nitrogen, 15 g of polyepichlorohydrin ("Gechron® 1000", product of Nippon Zeon Co., Ltd.) were dissolved in 135 g of N-methylpyrrolidone while stirring at 80° C. The solution was then chilled with ice water. A 50% aqueous solution of dimethylamine in an amount of 146 g was heated to 80° C., and dimethylamine gas generated was introduced into the autoclave to dissolve in the reaction solution while bubbling until the dimethylamine gas ceased to be generated. After the system was hermetically sealed to conduct a reaction at 120° C. for 12 hours, the system was opened to remove effluent gas. The reaction solution was cooled to room temperature and then subjected to reprecipitation in isopropyl ether in an amount 10 times of the reaction solution. The resultant precipitate was dissolved in ion-exchanged water, and the aqueous solution was subjected to a desalting treatment with a strongly basic ion-exchange resin ("IRA-402", product of Japan Organo Co., Ltd.) and then lyophilized, thereby obtaining an aminated polymer.

In a reaction vessel equipped with a reflux condenser, 23.34 g of sodium monochloroacetate were then suspended in 150 g of methanol. After 13.51 g of the aminated polymer were added to the suspension with stirring, a reaction was conducted for 24 hours under reflux of methanol. The reaction solution was cooled, and deposited insoluble matter was collected by filtration and then subjected to reprecipitation in a mixed solvent of ethanol/acetone (1/5 v/v) in an amount 10 times of the reaction solution. The resultant precipitate was dissolved in ion-exchanged water, and the aqueous solution was treated with a cation/anion mixed type ion-exchange resin ("IRA-120B"/"IRA-402", product of Japan Organo Co., Ltd.). The thus-treated aqueous solution was lyophilized to obtain 17.53 g of a polyether polymer. An NMR analysis revealed that this polymer is a polyoxyethylene-dimethylaminocarbobetaine polymer having the following structural units:

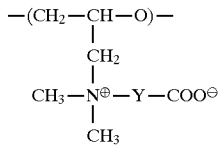

NMR (D$_2$O, 200 MHz, ppm): 3.27(6H,s, —N(C$\underline{H}_3$)$_2$), 3.5–4.34(7H,m, —C$\underline{H}_2$—CH—O—, —C$\underline{H}_2$—N$^+$—C$\underline{H}_2$—COO$^-$).

Molecular weight (GPC, 0.2M phosphate buffer, PEG standard): Mw=7,000; Mn=2,000.

Preparation Example 2

In a 0.5-liter reaction vessel, 15 g of polyepichlorohydrin rubber ("Gechron® 1000", product of Nippon Zeon Co., Ltd.) were dissolved in 135 g of N-methylpyrrolidone while stirring at 80° C. in a nitrogen stream. After 60.84 g of N-methylethanolamine were added to the solution, a reaction was conducted at 120° C. for 6 hours. The reaction solution was distilled at 110° C. under reduced pressure (5 mmHg) to remove a distillate, thereby obtaining a viscous substance. The resultant viscous substance was dissolved in ion-exchanged water, and the aqueous solution was subjected to a desalting treatment with a strongly basic ion-exchange resin ("IRA-402", product of Japan Organo Co., Ltd.) and then lyophilized, thereby obtaining an aminated polymer.

In a reaction vessel equipped with a reflux condenser, 28.3 g of sodium monochloroacetate were then suspended in 200 g of ethanol. After 21.3 g of the aminated polymer were added to the suspension, ion-exchanged water was added until the suspended sodium monochloroacetate was dissolved. After a reaction was conducted for 36 hours under reflux, the reaction solution was subjected to reprecipitation in a mixed solvent of acetone/methanol (2/1 v/v) in an amount 20 times of the reaction solution. The resultant precipitate was dissolved in ion-exchanged water, and the aqueous solution was subjected to a desalting treatment with a cation/anion mixed type ion-exchange resin ("IRA-120B"/"IRA-402", product of Japan Organo Co., Ltd.). The thus-desalted aqueous solution was lyophilized to obtain 21.9 g of a polyether polymer. An NMR analysis revealed that this polymer is a polyoxyethylene-methylhydroxyethylaminocarbobetaine polymer having the following structural units:

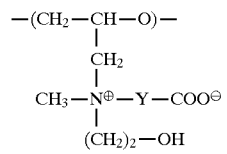

NMR (D$_2$O, 200 MHz, ppm): 2.95(3H,s, —N—C$\underline{H}_3$), 3.10–3.55(7H,m, —C$\underline{H}_2$—CH—O—, —C$\underline{H}_2$—N$^+$—C$\underline{H}_2$—CH$_2$—OH), 3.55–4.00(4H,m, —C$\underline{H}_2$—OH, —N$^+$—C$\underline{H}_2$—COO$^-$).

Molecular weight (GPC, 0.2M phosphate buffer, PEG standard): Mw=15,000; Mn=6,700.

Preparation Example 3

In an autoclave purged with nitrogen, 15 g of polyepichlorohydrin ("Gechron® 1000", product of Nippon Zeon Co., Ltd.) were dissolved in 135 g of N-methylpyrrolidone while stirring at 80° C. The solution was then chilled with ice water. A 50% aqueous solution of dimethylamine in an amount of 146 g was heated to 80° C., and dimethylamine gas generated was introduced into the autoclave to dissolve in the reaction solution while bubbling until the dimethylamine gas ceased to be generated. After the system was hermetically sealed to conduct a reaction at 120° C. for 12 hours, the system was opened to remove effluent gas. The reaction solution was cooled to room temperature and then subjected to reprecipitation in isopropyl ether in an amount 10 times of the reaction solution. The resultant precipitate was dissolved in ion-exchanged water, and the aqueous solution was subjected to a desalting treatment with a strongly basic ion-exchange resin ("IRA-402", product of Japan Organo Co., Ltd.) and then lyophilized, thereby obtaining an aminated polymer.

In a reaction vessel equipped with a reflux condenser, 13.5 g of the aminated polymer and 2.1 g of lauryl chloride were dissolved in 150 g of methanol to conduct a reaction for 12 hours under reflux. Then, 16.2 g of sodium monochloroacetate were added to the solution, followed by a reaction for 36 hours under reflux. The reaction solution was cooled, and deposited insoluble matter was collected by filtration and then subjected to reprecipitation in acetone in an amount 10 times of the insoluble matter. The resultant precipitate was dissolved in ion-exchanged water, and the aqueous solution was subjected to a desalting treatment with a cation/anion mixed type ion-exchange resin ("G-10", product of Japan Organo Co., Ltd.). The aqueous solution was titrated and neutralized to pH 7 using a pH meter, and then lyophilized, thereby obtaining 21.5 g of a polyether polymer. An NMR analysis revealed that this polymer is a polymer (a molar ratio, p/q between individual structural units p and q: 92.5/7.5) having the following structural units:

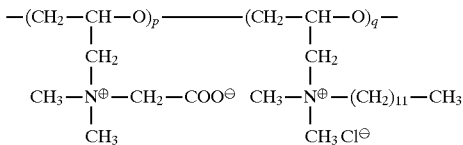

NMR (D$_2$O, 200 MHz, ppm): 0.78(3H,t, C$\underline{H}_3$—(CH$_2$)$_{11}$—), 1.19(20H,m,C$\underline{H}_3$—(CH$_2$)$_{10}$—C$\underline{H}_2$—), 3.78(8H,m, —N(C$\underline{H}_3$)$_2$, CH$_3$—(CH$_2$)$_{10}$—C$\underline{H}_2$—), 3.46–4.15(9H,m, —C$\underline{H}_2$—C$\underline{H}$—O—, C$\underline{H}_2$—N$^+$—C$\underline{H}_2$—COO$^-$), 4.15(2H,brs, —N$^+$—C$\underline{H}_2$—COO$^-$).

Molecular weight (GPC, 0.2M phosphate buffer, PEG standard): Mw=9,400; Mn=4,700.

Preparation Example 4

In a 0.5-liter reaction vessel, 15 g of polyepichlorohydrin rubber ("Gechron® 1000", product of Nippon Zeon Co., Ltd.) were dissolved in 135 g of N-methylpyrrolidone while stirring at 80° C. in a nitrogen stream. After 85.2 g of diethanolamine were added to the solution, a reaction was conducted at 125° C. for 6 hours. The reaction solution was cooled to room temperature and then subjected to reprecipitation in acetone in an amount 20 times of the reaction solution. The thus-obtained viscous substance was dissolved again in methanol, and the methanol solution was subjected to reprecipitation in ethyl acetate in an amount 10 times of the methanol solution. The resultant precipitate was dissolved in ion-exchanged water, and the aqueous solution was subjected to a desalting treatment with a strongly basic ion-exchange resin ("IRA-402", product of Japan Organo Co., Ltd.) and then lyophilized, thereby obtaining an aminated polymer.

In a reaction vessel equipped with a reflux condenser, 12.1 g of sodium monochloroacetate were then added to 120 ml of a mixed solvent of ethanol and water (2/1 v/v). After 11.2 g of the aminated polymer were added to the mixture, a reaction was conducted for 36 hours under reflux. The reaction solution was concentrated by means of an evaporator, and the concentrate was subjected to a desalting treatment with a cation/anion mixed type ion-exchange resin ("IRA-120B"/"IRA-402", product of Japan Organo Co., Ltd.). The thus-desalted aqueous solution was lyophilized. The thus-obtained polymer was dissolved in 200 ml of methanol, and the solution was subjected to reprecipitation in acetone in an amount 10 times of the solution. The resultant precipitate was lyophilized to obtain 8.6 g of a polyether polymer. An NMR analysis revealed that this polymer is a polymer having the following structural units:

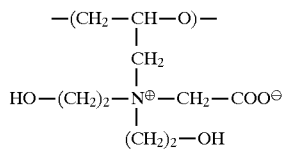

NMR (D$_2$O, 200 MHz, ppm): 3.15–4.15(15H,m, all protons). Molecular weight (GPC, 0.2M phosphate buffer, PEG standard): Mw=71,000; Mn=46,000.

Preparation Example 5

In a 0.5-liter reaction vessel, 40 g of glycidol were added dropwise to 210 g of a 40% aqueous solution of methylamine cooled with water over 2 hours, followed by the reaction of the reaction solution at 50° C for 5 hours in a nitrogen stream. The reaction solution was distilled at 70° C. under reduced pressure (5 mmHg) to remove a distillate, thereby obtained a secondary amine (glyceromonomethylamine). In a nitrogen stream, 15 g of polyepichlorohydrin ("Gechron® 1000", product of Nippon Zeon Co., Ltd.) were dissolved in 135 g of N-methylpyrrolidone while stirring at 80° C. After glyceromonomethylamine was added to the solution, a reaction was conducted at 125° C. for 24 hours. The reaction solution was then subjected to reprecipitation in hot acetone in an amount 20 times of the reaction solution, thereby obtaining a viscous substance. The viscous substance was dissolved in ion-exchanged water, and the aqueous solution was subjected to a desalting treatment with a strongly basic ion-exchange resin ("IRA-402", product of Japan Organo Co., Ltd.) and then lyophilized, thereby obtaining an aminated polymer.

In a reaction vessel, 20.6 g of sodium monochloroacetate were then added to 150 ml of a mixed solvent of ethanol and water (2/1 v/v). After 19 g of the aminated polymer were added to the mixture, a reaction was conducted for 36 hours under reflux. The reaction solution was subjected to reprecipitation in a mixed solvent of methanol/2-propanol (1/3 v/v) in an amount 10 times of the reaction solution. The resultant precipitate was dissolved in ion-exchanged water, and the aqueous solution was subjected to a desalting treatment with a cation/anion mixed type ion-exchange resin ("IRA-120B"/"IRA-402", product of Japan Organo Co., Ltd.). The thus-desalted aqueous solution was lyophilized to obtain 13 g of a polyether polymer. An NMR analysis revealed that this polymer is a polymer having the following structural units:

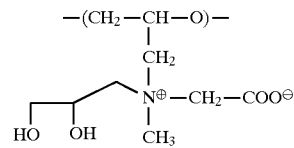

NMR (D$_2$O, 200 MHz, ppm): 3.1(3H,brs, —N—C$\underline{H}_3$), 3.4–4.1(12H,m, —C$\underline{H}_2$—C$\underline{H}$—O—,—C$\underline{H}_2$—N$^+$—C$\underline{H}_2$—COO$^-$, —C$\underline{H}_2$—CH(OH)—C$\underline{H}_2$—OH).

Molecular weight (GPC, 0.2M phosphate buffer, PEG standard): Mw=64,000; Mn=17,000.

Preparation Example 6

In an autoclave purged with nitrogen, 15 g of a poly (epichlorohydrin-glycidol) copolymer synthesized by controlling the functional group conversion rate of a polyepichlorohydrin in accordance with Journal of Polymer Science, Polymer Chemistry Edition, Vol. 13, 1993 (1975) were dissolved in 135 g of N-methylpyrrolidone while stirring at 80° C. The system was then chilled with ice water. A 50% aqueous solution of dimethylamine in an amount of 76 g was heated to 80° C., and dimethylamine gas generated was introduced into the autoclave to dissolve in the reaction solution while bubbling until the dimethylamine gas ceased to be generated. After the system was hermetically sealed to conduct a reaction at 120° C. for 12 hours, the system was opened to remove effluent gas. The reaction solution was cooled to room temperature and then subjected to reprecipitation in isopropyl ether in an amount 10 times of the reaction solution. The resultant precipitate was dissolved in ion-exchanged water, and the aqueous solution was subjected to a desalting treatment with a strongly basic ion-exchange resin ("IRA-402", product of Japan Organo Co., Ltd.) and then lyophilized, thereby obtaining an aminated polymer.

In a reaction vessel equipped with a reflux condenser, 8.53 g of sodium monochloroacetate were then suspended in 150 g of methanol. After 15 g of the aminated polymer were added to the suspension, a reaction was conducted for 24 hours under reflux of methanol. The reaction solution was cooled, and deposited insoluble matter was collected by filtration and then subjected to reprecipitation in acetone in an amount 10 times of the insoluble matter. The resultant precipitate was dissolved in ion-exchanged water, and the aqueous solution was subjected to a desalting treatment with a cation/anion mixed type ion-exchange resin ("IRA-120B"/ "IRA-402", product of Japan Organo Co., Ltd.). The desalted aqueous solution was lyophilized to obtain 10 g of a polyether polymer. An NMR analysis revealed that this polymer is a polymer (a molar ratio, p/q between individual structural units p and q: 90/10) having the following structural units:

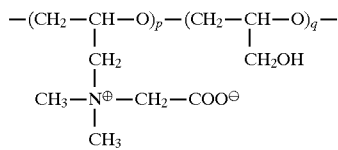

NMR ($D_2O$, 200 MHz, ppm): 3.27(6H,s, —N($\underline{CH}_3$)$_2$), 3.5–4.34(12H,m, —$\underline{CH}_2$—$\underline{CH}$—O—, —$\underline{CH}_2$—N$^+$—$\underline{CH}_2$—COO$^-$, —$\underline{CH}_2$—OH).

Molecular weight (GPC, 0.2M phosphate buffer, PEG standard):
Mw=5,500; Mn=3,400.

Preparation Example 7

In an autoclave purged with nitrogen, 15 g of a poly(epichlorohydrin-ethylene oxide-glyceryl glycidyl ether) copolymer obtained by treating a poly(epichlorohydrin-ethylene oxide-allyl glycidyl ether) copolymer ("Gechron® 3102", product of Nippon Zeon Co., Ltd.) with m-chloroperbenzoic acid/alkali were dissolved in 135 g of N-methylpyrrolidone while stirring at 80° C. The system was then chilled with ice water. A 50% aqueous solution of dimethylamine in an amount of 80.8 g was heated to 80° C., and dimethylamine gas generated was introduced into the autoclave to dissolve in the reaction solution while bubbling until the dimethylamine gas ceased to be generated. After the system was hermetically sealed to conduct a reaction at 120° C. for 12 hours, the system was opened to remove effluent gas. The reaction solution was cooled to room temperature and then subjected to reprecipitation in isopropyl ether in an amount 10 times of the reaction solution. The resultant precipitate was dissolved in ion-exchanged water, and the aqueous solution was subjected to a desalting treatment with a strongly basic ion-exchange resin ("IRA-402", product of Japan Organo Co., Ltd.) and then lyophilized, thereby obtaining an aminated polymer.

In a reaction vessel equipped with a reflux condenser, 8.53 g of sodium monochloroacetate were then suspended in 150 g of methanol. After 15 g of the aminated polymer were added to the suspension, a reaction was conducted for 24 hours under reflux of methanol. The reaction solution was cooled, and deposited insoluble matter was collected by filtration and then subjected to reprecipitation in acetone in an amount 10 times of the insoluble matter. The resultant precipitate was dissolved in ion-exchanged water, and the aqueous solution was subjected to a desalting treatment with a cation/anion mixed type ion-exchange resin ("IRA-120B"/ "IPA-402", product of Japan Organo Co., Ltd.). The desalted aqueous solution was lyophilized to obtain 8 g of a polyether polymer. An NMR analysis revealed that this polymer is a polymer (a molar ratio, p/q/r among individual structural units p, q and r: 47/48/5) having the following structural units:

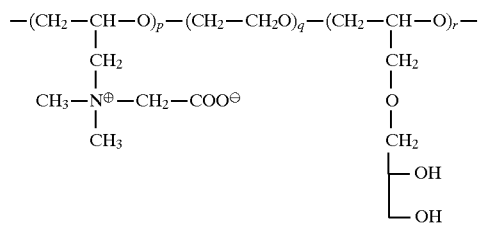

NMR ($D_2O$, 200 MHz, ppm): 3.27(6H,s, —N($\underline{CH}_3$)$_2$), 3.3–4.34(21H,m, —$\underline{CH}_2$—$\underline{CH}$—O—, —$\underline{CH}_2$—N$^+$—$\underline{CH}_2$—COO$^-$, —$\underline{CH}_2$—O—$\underline{CH}_2$—$\underline{CH}$(OH) — $\underline{CH}_2$—OH).

Molecular weight (GPC, 0.2M phosphate buffer, PEG standard): Mw=624,000; Mn=24,000.

Preparation Example 8

In a 0.5-liter reaction vessel, 15 g of polyepichlorohydrin rubber ("Gechron® 1000", product of Nippon Zeon Co., Ltd.) were dissolved in 135 g of N-methylpyrrolidone while stirring at 80° C. in a nitrogen stream. After 20.6 g of N-methylethanolamine were added to the solution, a reaction was conducted at 120° C. for 6 hours. The reaction solution was subjected to reprecipitation in a mixed solvent of ethyl acetate/hexane (1/1 v/v), thereby obtaining a viscous substance. The resultant viscous substance was dissolved in ion-exchanged water, and the aqueous solution was subjected to a desalting treatment with a strongly basic ion-exchange resin ("IRA-402", product of Japan Organo Co., Ltd.) and then concentrated under reduced pressure by means of an evaporator. The concentrate was then dissolved in methanol, and the methanol solution was subjected again to reprecipitation in a mixed solvent of ethyl acetate/hexane (1/1 v/v), thereby obtaining 19 g of an aminated polymer.

In a reaction vessel equipped with a reflux condenser, 15.35 g of sodium monochloroacetate were then suspended in 200 g of ethanol. After 19 g of the aminated polymer were added to the suspension with stirring, ion-exchanged water was added until the suspended sodium monochloroacetate was dissolved. After a reaction was conducted for 36 hours under reflux, the reaction solution was subjected to reprecipitation in a mixed solvent of acetone/ethanol (2/1 v/v) in an amount 10 times of the reaction solution. The resultant precipitate was dissolved in ion-exchanged water, and the aqueous solution was subjected to a desalting treatment with a cation/anion mixed type ion-exchange resin ("IRA-120B"/ "IRA-402", product of Japan Organo Co., Ltd.). The thus-desalted aqueous solution was lyophilized to obtain 20 g of a polyether polymer. An NMR analysis revealed that this polymer is a polymer (a molar ratio, p/q between individual structural units p and q: 90/10) having the following structural units:

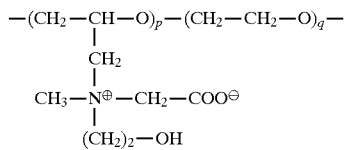

NMR (D$_2$O, 200 MHz, ppm): 2.95(6H,s, —N—CH$_3$), 3.10–3.55(11H,m, —C$\underline{H}_2$—CH—O—, —C$\underline{H}_2$—N$^+$—C$\underline{H}_2$—CH$_2$—OH), 3.55–4.00(4H,m, —N$^+$—CH$_2$—C$\underline{H}_2$—OH, —N$^+$—C$\underline{H}_2$—COO$^-$).

Molecular weight (GPC, 0.5 wt. % aqueous solution, 50 mM LiBr, PEG standard): Mw=663,000; Mn=30,000.

Preparation Example 9

An autoclave purged with nitrogen was charged with 15 g of polyepichlorohydrin ("Gechron® 1000", product of Nippon Zeon Co., Ltd.), 6.1 g of sodium sulfite and 100 g of ion-exchanged water. After the system was hermetically sealed to conduct a reaction at 150° C. for 10 hours, the system was opened to distill off the ion-exchanged water. The reaction system was purged with nitrogen, and 135 g of N-methyl-pyrrolidone were added to the residue. Dimethylamine (gas) was introduced into the autoclave to dissolve in the reaction solution. After the system was hermetically sealed to conduct a reaction at 120° C. for 10 hours, the system was opened to remove effluent gas. After the reaction solution was cooled to room temperature, and the resultant precipitate was collected by filtration, the precipitate was subjected to reprecipitation in isopropyl ether in an amount 10 times of the precipitate. The resultant precipitate was dissolved in ion-exchanged water, and the aqueous solution was subjected to a desalting treatment with a strongly basic ion-exchange resin ("IRA-402", product of Japan Organo Co., Ltd.) and then lyophilized, thereby obtaining 10 g of an aminated polymer.

In a reaction vessel equipped with a reflux condenser, 15.35 g of sodium monochloroacetate were then suspended in 200 g of ethanol. After 10 g of the aminated polymer were added to the suspension with stirring, ion-exchanged water was added until the suspended sodium monochloroacetate was dissolved. After a reaction was conducted for 36 hours under reflux, the reaction solution was subjected to reprecipitation in acetone in an amount 10 times of the reaction solution. The resultant precipitate was dissolved in ion-exchanged water, and the aqueous solution was then lyophilized to obtain 9 g of a polyether polymer. An NMR analysis revealed that this polymer is a polymer (a molar ratio, p/q between individual structural units p and q: 90/10) having the following structural units:

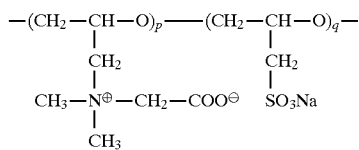

NMR (D$_2$O, 200 MHz, ppm): 2.95(2H,brs, —C$\underline{H}_2$—SO$_3$Na), 3.27 (6H,s, —N$^+$(C$\underline{H}_3$)$_2$), 3.5–4.34(7H,m, —C$\underline{H}_2$—CH—O, —C$\underline{H}_2$—N$^+$—C$\underline{H}_2$—COO$^-$).

Molecular weight (GPC, 0.5 wt. % aqueous solution, 50 mM LiBr, PEG standard): Mw=3,000; Mn=2,200.

Preparation Example 10

In an autoclave purged with nitrogen, 15 g of polyepichlorohydrin ("Gechron® 1000", product of Nippon Zeon Co., Ltd.) were dissolved in 200 g of N-methylpyrrolidone while stirring at 50° C. The solution was then chilled with ice water. A 50% aqueous solution of dimethylamine in an amount of 146 g was heated to 80° C., and dimethylamine gas generated was introduced into the autoclave to dissolve in the reaction solution while bubbling until the dimethylamine gas ceased to be generated. After the system was hermetically sealed to conduct a reaction at 120° C. for 12 hours, the system was opened to remove effluent gas. The reaction solution was cooled to room temperature and then subjected to reprecipitation in isopropyl ether in an amount 10 times of the reaction solution. The resultant precipitate was dissolved in ion-exchanged water, and the aqueous solution was subjected to a desalting treatment with a strongly basic ion-exchange resin ("IRA-402", product of Japan Organo Co., Ltd.) and then lyophilized, thereby obtaining an aminated polymer.

In a reaction vessel purged with nitrogen, 13.51 g of the aminated polymer were dissolved in 150 g of absolute ethanol to keep the temperature of the solution at 35° C. To the solution, 7.4 g of β-propiolactone were added, thereby conducting a reaction at 35° C. for 6 hours. The resultant precipitate was collected by filtration, dissolved in water and then subjected to reprecipitation in a mixed solvent of ethanol/acetone (1/2 v/v) in an amount 10 times of the aqueous solution. The resultant precipitate was dissolved in ion-exchanged water, and the aqueous solution was treated with a cation/anion mixed type ion-exchange resin ("IRA-120B"/"IRA-402", product of Japan Organo Co., Ltd.) and lyophilized, thereby obtaining 14.60 g of a polyether polymer. An NMR analysis revealed that this polymer is a polyoxyethylene-dimethylaminocarbobetaine polymer having the following structural units:

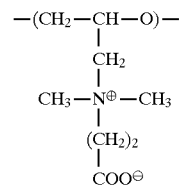

NMR (D$_2$O, 200 MHz, ppm): 3.7(6H, s, —N(C$\underline{H}_3$)$_2$), 3.5–4.34(9H,m, —C$\underline{H}_2$—CH—O—, —C$\underline{H}_2$—N$^+$—(C$\underline{H}_2$)$_2$—COO$^-$).

Molecular weight (GPC, 0.2M phosphate buffer, PEG standard): Mw=20,000; Mn=15,000.

Test Example 1

With respect to individual ingredients shown in Table 1, the moisture retention and the feeling upon use were evaluated. The results are shown in Table 1.

(Evaluation Methods)

Moisture retention

A 0.5% aqueous solution of each sample is prepared, applied to a human antecubital site air-conditioned at 20° C. and 40% humidity in a proportion of 10 μl per cm$^2$ and left to stand for 10 minutes. Before and after this treatment, the epidermal conductance of the applied site is measured by means of a "SKICON-200" (manufactured by IBS Company) to determine the moisturizing ability of the sample. The moisturizing ability is expressed in terms of a ratio of the conductance after the treatment to the conductance before the treatment.

The above procedure is repeated 10 times, and their average value is regarded as a measurement result.

Besides, the treated site is rinsed with running water and dried with a towel. Upon elapsed time of 10 minutes after the drying, its epidermal conductance is measured in the same manner as described above, thereby determining the moisturizing ability after the rinsing. The moisturizing ability after the rinsing is expressed in terms of a ratio of the conductance after the rinsing to the conductance before the treatment. Feeling upon use:

A 5% aqueous solution of potassium myristate containing 0.2% of each sample is prepared. After 2 ml of the solution are dropped on the palm of a hand to cause it to thoroughly lather, the hands are rinsed with running water and dried with a towel. After about 5 minutes, the feeling given to the palms is evaluated in accordance with the following standard:

Moisturized feeling:

o: Giving a moisturized feeling;

Δ: Somewhat giving a moisturized feeling;

x: Giving no moisturized feeling.

Stickiness to the touch:

o: Not sticky to the touch;

Δ: Not very sticky to the touch;

x: Sticky to the touch.

TABLE 1

|  | Moisturizing ability | Moisturizing ability after rinsing | Feel upon use | |
| --- | --- | --- | --- | --- |
|  |  |  | Moisturized feeling | Sticky feel |
| Invention product: | | | | |
| 1 Compound of Preparation Example 2 | 1.6 | 1.6 | o | o |
| 2 Compound of Preparation Example 3 | 1.5 | 1.5 | o | o |
| 3 Compound of Preparation Example 5 | 1.6 | 1.6 | o | o |
| 4 Compound of Preparation Example 7 | 1.5 | 1.5 | o | o |
| Comparative product: | | | | |
| 1 Blank (water) | 1.0 | 1.0 | x | o |
| 2 Glycerol | 1.7 | 1.2 | Δ | Δ |
| 3 Cationized cellulose | 1.3 | 1.3 | Δ | x |

As apparent from the results shown in Table 1, it is understood that all the invention products have excellent moisturizing ability, which is kept up even after the rinsing, give users a pleasant moisturized feeling and are not sticky to the touch.

Formulation Example 1

(Pasty face cleanser)

A pasty face cleanser having the following composition was prepared in accordance with a method known per se in the art.

The resulting face cleanser gave a refreshed feeling after washing and kept up the moisturized feeling.

| (Composition) | (%) |
| --- | --- |
| Sodium sesquilauryl phosphate | 25 |
| Dipotassium myristyl sulfosucinate | 5 |
| Cocoyldiethanolamide | 2 |
| Polyethylene glycol monostearate | 4 |
| Hydroxyethylmethylbetaine-polyeter polymer (compound of Preparation Example 2) | 0.5 |
| Carboxyvinyl polymer | 0.5 |
| Paraben | 0.2 |
| Perfume base | 0.3 |
| Purified water | Balance. |

Formulation Example 2

(Body shampoo)

A body shampoo having the following composition was prepared in accordance with a method known per se in the art.

The resulting body shampoo gave no dry skin even after washing and kept up the moisturized feel.

| (Composition) | (%) |
| --- | --- |
| Triethanolamine sesquilauryl phosphate | 25 |
| Decyl polyglucoside | 5 |
| Sodium lauroylsarcosinate | 5 |
| Propylene glycol | 5 |
| Dimethylbetaine-polyoxyethylene-diglyceryl ether-polyether copolymer (compound of Preparation Example 7) | 0.5 |
| Octaglyceryl monooleate | 0.2 |
| Perfume base | 0.3 |
| Purified water | Balance. |

Formulation Example 3

(Shampoo)

A shampoo having the following composition was prepared in accordance with a method known per se in the art.

The resulting shampoo gave no creaky feeling upon shampooing and rinsing, was not sticky to the touch and gave a moisturized feeling after shampooing, and kept up the moisturized feeling.

| (Composition) | (%) |
| --- | --- |
| Lauryldimethylamine acetate betaine | 10 |
| Sodium N-lauroyl glutamate | 10 |
| Ethylene glycol distearate | 2 |
| Ethylcarbitol | 2 |
| Hydroxyethylmethylbetaine-polyeter polymer (compound of Preparation Example 2) | 1 |
| Perfume base | 0.5 |
| Purified water | Balance. |

Formulation Example 4

(Hair treatment)

A hair treatment having the following composition was prepared in accordance with a method known per se in the art.

The resulting hair treatment was excellent in a softness-imparting effect on the hair and not sticky to the touch, gave a moisturized feeling, and kept up the feeling.

| (Composition) | (%) |
|---|---|
| Stearyl alcohol | 5 |
| Polypeptide (hydrolyzate of collagen) | 5 |
| Stearyltrimethylammonium chloride | 3 |
| Liquid paraffin | 3 |
| Hydroxyethylmethylbetaine-polyeter polymer (compound of Preparation Example 2) | 2 |
| Ethylcarbitol | 1 |
| Perfume base | 0.5 |
| Purified water | Balance. |

Formulation Example 5

(Lotion)

A lotion having the following composition was prepared in accordance with a method known per se in the art.

The resulting lotion was not sticky to the touch, gave a moisturized feeling, had sufficient moisture retention hardly being washed away by sweat and kept up the moisturized feeling.

| (Composition) | (%) |
|---|---|
| Ethanol | 10 |
| Glycerol | 5 |
| Polyoxyethylene (20) oleyl ether | 1 |
| Sodium lactate | 0.6 |
| Lactic acid | 0.2 |
| Hydroxyethylmethylbetaine-polyeter polymer (compound of Preparation Example 2) | 0.2 |
| Perfume base | 0.3 |
| Purified water | Balance. |

Formulation Example 6

(Bath additive composition)

A bath additive composition having the following composition was was prepared in accordance with a method known Per se in the art.

The resulting bath additive composition was excellent in a moisturizing effect on the skin, gave a moisturized feeling and kept up the feeling.

| (Composition) | (%) |
|---|---|
| Sodium hydrogencarbonate | 66 |
| Dextrin | 30 |
| Hydroxyethylmethylbetaine-polyeter polymer (compound of Preparation Example 2) | 3 |
| Perfume base | 0.5 |
| Coloring matter | 0.5. |

INDUSTRIAL APPLICABILITY

The polyether polymers according to the present invention are excellent in moisture retention (water retention), adsorptivity and hydrophilicity, and cosmetic and detergent compositions containing these polymers keep up an excellent moisturizing effect over a long period of time and give a pleasant feeling.

We claim:

1. A polyether polymer having structural units represented by the following general formula (1):

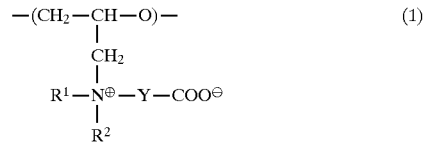

wherein R1 and R2 mean individually an alkyl group of 1–20 carbon atoms, which may have one or more hydroxyl groups, and Y denotes an alkylene group of 1–10 carbon atoms, which may have a hydroxyl group; said polyether polymer having a weight-average molecular weight of 5,000–1,000,000.

2. The polyether polymer according to claim 1, wherein said structural unit is represented by the following formula (a), (b), (c) or ( d):

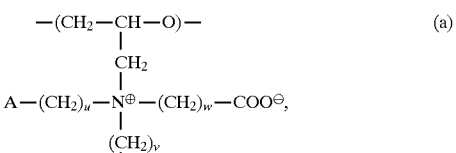

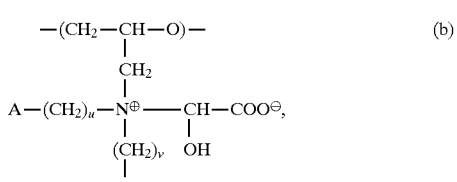

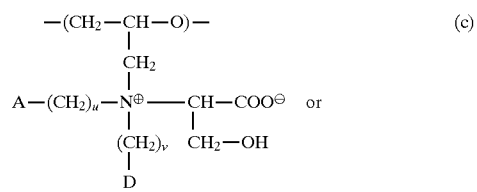

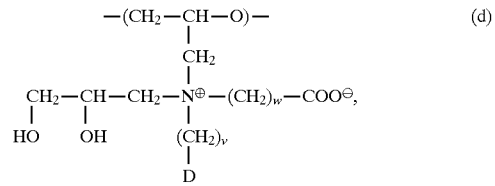

wherein A and D mean, independently of each other, a hydrogen atom or a hydroxyl group, u and v are, independently of each other, a number of 1–20, and w is a number of 1–10.

3. The polyether polymer according to claim 1, wherein said structural unit represented by the general formula (1) is represented by the following formula (a-1), (a-2), (a-3) or (d-1):

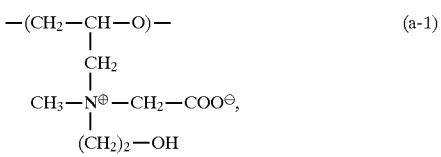

-continued

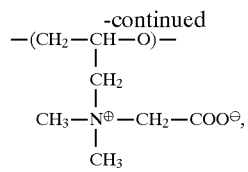 (a-2)

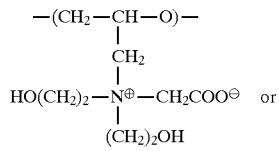 (a-3)

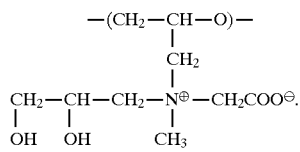 (d-1)

4. The polyether polymer according to claim 1, which further has one or more kinds of structural units selected from those represented by the following formulae (e) to (i):

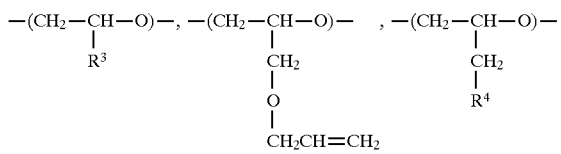

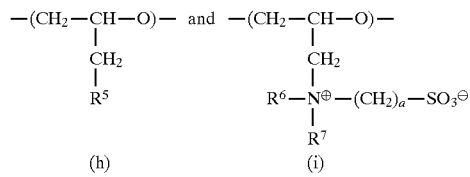

(h)    (i)

wherein in the formula (e), $R^3$ means —H, —$CH_3$, —$CH_2OH$, —$CH_2$—O—$CH_2CH(OH)$—$CH_2OH$, —$CH_2OR^8$, —$CH_2SR^8$ or —$CH_2S(CH_2)_3SR^8$ in which $R^8$ is an alkyl, alkenyl, cycloalkyl, aralkyl or aryl group having 1–20 carbon atoms; in the formula (g), $R^4$ denotes a cationic group represented by the following formula (g-1), (g-2) or (g-3):

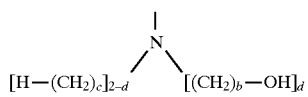 (g-1)

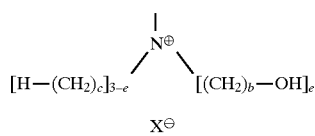 (g-2)

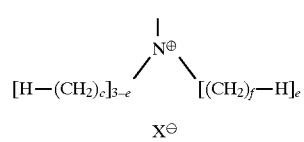 (g-3)

wherein b and c are individually a number of 1–10, is a number of 0–2, e is a number of 0–3, f is a number of 1–20, and $X^-$ denotes a counter anion; in the formula (h), $R^5$ means —$SO_3M$ or —O—$CH_2$—COOM in which M is a metal ion or a hydrogen atom; and in the formula (i), $R^6$ and $R_7$ mean individually an alkyl group of 1–20 carbon atoms, which may have one or more hydroxyl groups, and a is a number of 1–10.

5. A process for preparing a polyether polymer having structural units represented by the general formula (1):

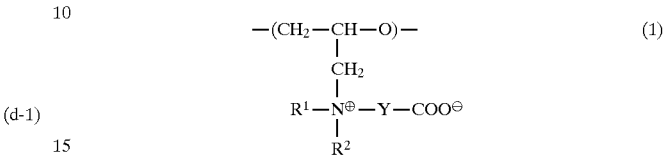 (1)

wherein R1 and R2 mean individually an alkyl group of 1–20 carbon atoms, which may have one or more hydroxyl groups, and Y denotes an alkylene group of 1–10 carbon atoms, which may have a hydroxyl group, said polyether polymer having a weight-average molecular weight of 5,000–1,000,000, which process comprises reacting a polymer having structural units represented by the general formula (2):

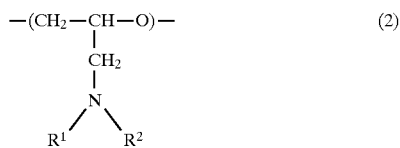 (2)

wherein $R^1$ and $R^2$ have the same meaning as defined above, with a ω-halocarboxylic acid or a salt thereof represented by the following general formula (3) or a cyclic lactone represented by the following general formula (4):

$$Z-Y-COOM \quad (3)$$

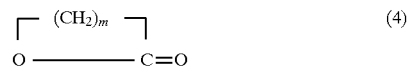 (4)

wherein Y has the same meaning as defined above, Z denotes a halogen atom, M is a metal ion or a hydrogen atom, and m stands for a number of 1–8.

6. A moisturizer comprising, as an active ingredient, the polyether polymer according to claim 1.

7. A cosmetic composition comprising the polyether polymer according to claim 1.

8. A detergent composition comprising the polyether polymer according to claim 1 and detergent ingredients.

9. A detergent composition comprising the polyether polymer according to claim 1 and detergent ingredients.

10. A detergent composition comprising the polyether polymer according to claim 1 and detergent ingredients.

* * * * *

UNITED STATES PATENT AND TRADEMARK OFFICE
CERTIFICATE OF CORRECTION

PATENT NO. : 5,853,611

DATED : December 29, 1998

INVENTOR(S): Hiroshi Kawamukai, et al.

It is certified that an error appears in the above-identified patent and that said Letters Patent is hereby corrected as shown below:

Column 23, Line 61, "a number of 1-10," should read --a number of 1-10, d--.

Column 24, Lines 56 and 57, "9. A detergent composition comprising the polyether polymer according to claim 1 and detergent ingredients." should read --9. A method of moisturizing hair and/or skin, comprising applying the polyether polymer according to claim 1 to skin and/or hair.--

Column 24, Lines 58 and 59, delete Claim 10. in its entirety.

Signed and Sealed this

Twelfth Day of October, 1999

Attest:

Q. TODD DICKINSON

Attesting Officer

Acting Commissioner of Patents and Trademarks